United States Patent [19]

von Nostitz

[11] 4,337,042
[45] Jun. 29, 1982

[54] DENTAL ARRANGEMENT AND PROCESS FOR MANUFACTURING DENTURES

[76] Inventor: Frauke H. F. von Nostitz, Allescherstrasse 45, 8000 Munich 71, Fed. Rep. of Germany

[21] Appl. No.: 194,332

[22] Filed: Oct. 6, 1980

[30] Foreign Application Priority Data

Oct. 17, 1979 [DE] Fed. Rep. of Germany ....... 2942062

[51] Int. Cl.³ ............................................ A61C 13/22
[52] U.S. Cl. ................................... 433/171; 433/191; 433/196
[58] Field of Search ............... 433/171, 167, 190, 191, 433/196, 199, 213

[56] References Cited

U.S. PATENT DOCUMENTS

| | | | |
|---|---|---|---|
| 2,618,062 | 11/1952 | Hendricks | 433/191 |
| 3,846,911 | 11/1974 | Wichner | 433/171 |
| 4,184,253 | 1/1980 | Tureaud | 433/171 |

FOREIGN PATENT DOCUMENTS

| | | | |
|---|---|---|---|
| 1098670 | 2/1961 | Fed. Rep. of Germany | 433/171 |
| 1813332 | 6/1970 | Fed. Rep. of Germany | 433/191 |
| 2226148 | 11/1974 | France | 433/171 |
| 2381513 | 10/1978 | France | 433/191 |

*Primary Examiner*—Gene Mancene
*Assistant Examiner*—John J. Wilson
*Attorney, Agent, or Firm*—Browdy and Neimark

[57] ABSTRACT

An arrangement of artificial teeth, preferably made of methacrylate, in which the teeth are mounted at the roots end in the natural sequence on a flexible plastic strip made of acrylate plastic in such manner that movement of the teeth in relation to each other is possible without their disengagement from said plastic strip. The arrangement is suitable for the manufacture of an artificial partial or total denture, in that on a preformed prosthesis in which a part of the teeth can already be contained on the complete prosthesis base, a fixing substance is applied to the free remaining part of said prosthesis base, and the dental arrangement is fitted into it.

6 Claims, 1 Drawing Figure

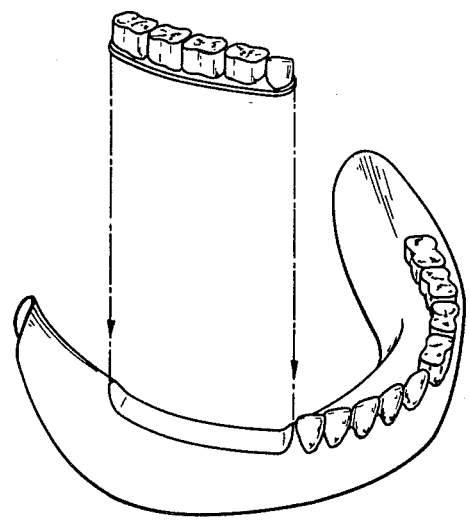

DENTAL ARRANGEMENT AND PROCESS FOR MANUFACTURING DENTURES

BACKGROUND OF THE INVENTION

This invention relates to a dental arrangement comprising at least two artificial teeth, preferably made of methacrylate, as well as a process for the manufacture of an artificial denture, especially while using this dental arrangement.

The manufacture of artificial teeth and of prostheses which contain them is known. Processes for the manufacture of dental prostheses are described e.g. in German DE-PS No. 974 046 and in DE-OS No. 22 13 364. While these known methods for the manufacture of artificial teeth and prostheses require a certain expenditure, recently consideration has been given to making available to the dentist fully prefabricated instant prostheses. The latter comprise preformed, complete rows of teeth made of a plastic base which can be fitted in only one or two sessions. Due to the lower costs of such prefabricated instant prostheses it is possible at a very early stage to make available to the patient a "transitional denture". Moreover the opportunity arises to lower perceptibly the costs of prostheses which are made conventionally for those who do not place such great stress on the luxury of dentures made by the conventional methods.

Individual artificial teeth are also offered by the trade, made either on the basis of porcelain or of plastic, the latter being usually made on the basis of methacrylate. Such artificial teeth are available either singly or in the form of collections, in which the teeth can be removed individually and are arranged either in appropriate containers or on wax.

Despite their manifold advantages fully prefabricated instant prostheses have not as yet made much headway in practice. The reasons for this lie especially in the fact that the prostheses containing complete rows of teeth in their natural sequence do not lead to a satisfactory occlusion. If when the prosthesis is being fitted and inserted with lining, attention is paid to the requisite superimposition of the molars, there is very often a resultant so-called "over-occlusion". But if the prosthesis is so fitted that the teeth in the frontal area provide normal occlusion, vice-versa the result is often a defective superimposition of the molars. This unsatisfactory situation has already given cause for the sale of instant prostheses, in which the number of the molars is reduced as compared with the normal state. Even though the discomfort arising from occlusion is hereby reduced, the patient still feels in the back area of the jaws the resultant bite on the plastic base.

The invention is based on the object of avoiding the problem described above when fitting several artificial teeth. A special object of the invention is on the one hand to simplify the work by making a dental arrangement available to the dental technicians or to the dentists and thereby to make possible a reduction in costs, and on the other hand to contribute to the optimal fitting of artificial teeth. It is especially intended that the insertion of prefabricated instant prostheses should be perfected by an improvement in their fitting.

These objects are attained by the creation of a dental arrangement of the type described above, which is characterized in that the teeth are mounted on the roots side in the natural sequence on a flexible plastic strip in such manner that the relative movement of the teeth is possible without their disengagement from the said plastic strip.

By using such a dental arrangement, the processes for the manufacture of artificial dentures and especially of instant prostheses, which can in the first phase be made using a reduced number of teeth, can be decisively improved.

By the phrase "natural sequence" what is meant is the sequence of the teeth in the mouth, so that the dental arrangement usually comprises the natural sequence of two or more teeth which correspond to a section of the natural rows of teeth.

The plastic strips on which the teeth are mounted are normally a band, a striate, or a connecting substance made of plastic, which enable a relative motion of the teeth without their disengagement from the plastic strip. It is particularly advantageous if movement of the artificial teeth both in the vertical and in the horizontal directions is possible. It is better to arrange the teeth with their lower sides, i.e. "root sides" on the band or strip of plastic, which hereinafter is designated the plastic strip for the sake of convenience. It is also certainly possible to arrange the teeth on a strip or band of another material in a manner allowing relative motion, e.g. with a gauze wire. But this is less preferable because the use of other support materials generally involves higher manufacturing costs and also frequently a worse compatibility with the prosthesis base of plastic, in which the dental arrangement is fixed.

The application of the teeth on the plastic strip should in particular be so mobile and flexible that a motion of the teeth relative to each other is possible as far as possible both horizontally and vertically when fitting the plastic strip onto a prefabricated dental prosthesis, e.g. by biting. Due to the possible movement of the teeth relative to each other, which are secured on a band, striate or on a strip, when the fitting is carried out, an optimal position of the teeth in the local areas of the prefabricated instant prosthesis can be achieved, by means of which the feared overlap is easily avoidable and the occlusion is attainable. As a result of the fitting process, the teeth which are arranged in their natural sequence in the dental arrangement can assume the position which will avoid the above-mentioned inaccuracies when biting.

The artificial teeth contain preferably one or more recesses on their lower sides, e.g. a notch in which the plastic strip can advantageously be guided without substantial contact with the side surfaces of the teeth.

The dental arrangement can comprise any sections of the teeth desired. As a rule they consist of at least two and maximally about 6 to 8 teeth, since otherwise the advantages attainable, especially with regard to the fitting on the instant prosthesis, are no longer fully ensured. Preferably the dental arrangement according to the invention contains for example the molar part of a prosthesis, which may optionally include the adjoining canine tooth. Such a dental arrangement can be used advantageously on an instant prosthesis, in which the entire base and all the teeth with the exception of the molars are contained. In another preferred embodiment of the invention the dental arrangement contains the front teeth, optionally including one or both of the adjacent canines, which then, with the use of a prefabricated instant prosthesis without the part for front teeth, leads to an optimal artificial denture which is easily made.

It is especially favorable if the plastic of the strip is compatible with the plastic located on the upper side of the dental prosthesis base and/or with the embedding plastic. In this manner an optimal bonding of the teeth supplied by the dental arrangement with the plastic base or plastic bed of the prefabricated instant prosthesis becomes possible.

In a further preferred embodiment of the invention, the plastic of the strip is flexible and/or remains soft. This provides an especially good mobility for the teeth, which however do not lose their relative sequence during the fitting process. The plastic of the strip is generally an acrylate plastic, or it contains a decisive proportion thereof. In addition ancillary substances such as stabilizers, fillers, etc. may be present, which are already known to the expert.

This acrylate plastic is preferably an acrylic or methacrylic acidic ester with a total of 6 to 10 carbon atoms or a mixture thereof. But the lower esters of the named acrylic or methacrylic acid are usable, as are also the ester derivates with more than 10 carbon atoms, which can be used depending on the type of prosthesis base plastic. A preferable ester according to the invention is acrylic or methacrylic acid-hexylester, whereby the hexyl component can also be cyclical.

In order to achieve good flexibility but also the toughness of the selected ester components it is often advisable to insert a certain proportion of softener. Suitable softeners are for example alkyl sulfonic acid esters of the phenol (e.g. "Mesamoll" from Bayer AG).

The arrangement according to the invention is especially suitable for the manufacture of artificial dentures while using conventional instant prostheses, which however have to have a number of teeth reduced by the dental arrangement. It is advantageous that the dental arrangement of the invention should comprise the molar tooth part, with or without the canine tooth, whereby in this case a prefabricated prosthesis with the complete number of firmly embedded teeth, which is reduced by the molar teeth part, is used. In the process according to the invention for the manufacture of an artificial denture, on the above mentioned prosthesis, in which at least a part of the teeth is already contained on the complete prosthesis base, a fixing substance is applied to the free remaining part of the prosthesis base, and in it one or more of the dental arrangements according to the invention, containing the still missing teeth in their natural sequence, are then fitted. Optionally thereafter a further rapid hardening acrylate plastic can be applied to obtain a better fit of the teeth or it may be applied for reasons of appearance between or laterally on the teeth.

It is here advantageous to use those instant prostheses which are recessed in the area of the intended insertion, or have been otherwise prepared to improve the insertion and the adhesion. The manufacture of instant prostheses per se is known. In general they are made in a two-stage process whereby the lower part of the prosthesis base is made of a more flexible methacrylate plastic, e.g. methyl methaacrylate, with a proportion of a softener. On this is placed a more rigid and mechanically more stable layer of methacrylate which is either free of or contains little softener, frequently methyl methacrylate, which is heat polymerized, while the teeth are fully mounted in this upper material. In the process of the invention such a prosthesis can be used with advantage, in which a part of the teeth are not contained. This part is usually either the molar part and/or the front part.

Proceeding from this basis for the previously known prosthesis especially good results can be achieved in the process of the invention if the material of the dental strip is also composed of acrylic acid or the methacrylic acidic ester. Especially favorable are compounds such as those having more than 6 carbon atoms, while the n-hexyl- or cyclohexyl esters, as well as t-butyl- or epoxypropylester are especially preferred. In addition proportions of mixed polymer, filler, stabilizer, dyes, and other known ancillary substances can be used. But it is important that a good fixture of the teeth on the strip be attained while permitting movement of the teeth relative to each other during fitting is possible. The dental arrangement according to the invention is inserted on the above-mentioned prosthesis in that a rapid-hardening substance is applied to the correspondingly prepared "vacant space". This rapid-hardening substance is preferably composed of a plastic material base which also forms the upper part of the prosthesis base. Therefore in general as the fixing substances, i.e. jellies or pastes or other spreadable or mouldable substances are used on the basis of monomer acrylic or methacrylic acidic esters, which can harden in the manner known per se with the addition of hardeners and catalysts. Before the hardening the dental arrangement is impressed into place, having the teeth in the natural sequence. By fixing the teeth in the natural sequence a simultaneous fitting of a number of teeth can be achieved, without the latter being too much displaced relatively to each other during the fitting process. On the other hand it is possible that the teeth, due to the flexibility of the strip, will assume the individual position which is necessary to obtain occlusion. The insertion of the dental arrangement of the invention, which can be simply produced on an industrial scale, is therefore uncomplicated and the use of prefabricated prostheses is thereby made possible for the first time in many cases.

The fitting process of the dental arrangement in the plastic base of the prosthesis can be done in the manner known per se. Due to the existing "counter-teeth" or to an optionally-inserted wax strip, the position of the teeth and the so-called "bite" is determined in the manner desired.

Due to the dental arrangement of the invention it is possible to obtain the advantages of a prefabricated prosthesis into which a prefabricated part is fitted, while simultaneously an individual fitting and an optimal bite are attainable.

The dental arrangement of the invention is indicated in the enclosed schematic drawing. It shows very well that it is adequate for the plastic strips to cover the teeth only on a small part of their lower surface. When using a suitable soft-elastic or a tough plastic, such as e.g. the higher esters of acrylic acid and methacrylic acid really good bonding of the teeth, which allow relative movement to each other during the fitting process, can be achieved. From the drawing it is also discernible that the manufacture of the dental arrangement of the invention can be made very simple, e.g. by inserting the artificial teeth in the still soft, not yet hardened plastic mass, which can be located in a mold etc.

What is claimed is:

1. Dental arrangement for the manufacture of an artificial partial or total denture comprising at least two artificial teeth connected in natural sequence, characterized in that the artificial teeth are mounted along the roots side on a strip made of a plastic selected from acrylic or methacrylic esters which are flexible or remain soft in such a manner that the relative movement of the teeth with respect to one another horizontally as well as in the vertical direction is possible without disengagement of the teeth from the plastic strip.

2. Dental arrangement according to claim 1, characterized in that the plastic of the strip is compatible with a plastic located on the upper side of a dental prosthesis and/or with an embedding plastic.

3. Dental arrangement according to claim 1 or 2, characterized in that the acrylic or methacrylic ester has a total of more than 6 carbon atoms.

4. Dental arrangement according to claim 3, characterized in that the ester is a hexyl ester.

5. Process for the manufacture of an artificial partial or total denture consisting essentially of the steps of:
  applying, on an already prepared prosthesis, in which a part of the teeth may already be contained on the complete prosthesis base, a first fixing substance to the free remaining portion of the prosthesis base;
  fitting in said first fixing substance one or more dental arrangements, which contain the missing teeth in their natural order, the missing teeth being mounted on the roots side on a strip made of an acrylic or methacrylic ester plastic which is flexible or remains soft, in such a manner that relative movement of the teeth with respect to one another, horizontally as well as in the vertical direction, is possible without disengagement of the teeth from the prosthesis base; and
  applying a second fixing substance which hardens around the fitted dental arrangement.

6. A process according to claim 5, wherein said second fixing substance is a rapid-hardening substance of monomer acrylic or methacrylic acidic ester which hardens around the fitted dental arrangement.

* * * * *